United States Patent [19]
Bruchmann

[11] Patent Number: 6,053,915
[45] Date of Patent: Apr. 25, 2000

[54] EXTERNAL TUTOR FOR THE TREATMENT OF RADIUS DISTAL END FRACTURES

[76] Inventor: Guillermo Victorio Bruchmann, Maipu 723 5° floor, Rosario 2000. Santa Fe Province, Argentina

[21] Appl. No.: 09/145,632

[22] Filed: Sep. 2, 1998

[51] Int. Cl.[7] .................................................. A61B 17/60
[52] U.S. Cl. .............................................. 606/54; 606/59
[58] Field of Search .................................. 606/54, 55, 57, 606/59

[56] References Cited

U.S. PATENT DOCUMENTS

| | | | |
|---|---|---|---|
| 4,548,199 | 10/1985 | Agee | 128/92 |
| 4,611,586 | 9/1986 | Agee et al. | 128/92 |
| 5,803,924 | 9/1998 | Oni et al. | 606/54 |
| 5,810,813 | 9/1998 | Faccioli et al. | 606/55 |

Primary Examiner—Michael Buiz
Assistant Examiner—Daphna Shai
Attorney, Agent, or Firm—Dority & Manning, P.A.

[57] ABSTRACT

The present invention refers to an external tutor for treating fractures in the radius distal end, said type of external tutor contemplates the use of longitudinal pins to be inserted in the bone structure. Its main advantage is that it provides stiffness and stability to the fractured zone, allowing, in turn, a higher mobility if compared to traditional resources. It consists of a planar and elongated part, comprising a body and a head articulated to it. Both the head and the body have orifices which are run through by the pins, which are withheld by pressure fitting-up bolts integrally lodged into threaded orifices matching said orifices through which the pins run through. Since the passing orifices in the head are oblique, both the pins and the tutor as a whole define a structure of triangular conformation.

6 Claims, 3 Drawing Sheets

EXTERNAL TUTOR FOR THE TREATMENT OF RADIUS DISTAL END FRACTURES

BACKGROUND AND SUMMARY OF THE INVENTION

The present invention generally relates to an external tutor for the treatment of fractures in the radius distal end, whereby it is possible to effectively treat said fractures without having to puncture the lower radio cubital articulation.

More specifically, the present invention relates to the functional and construction characteristics of a particular external tutor capable of being used as a fastening auxiliary resource during the treatment of the bone fractures mentioned above.

The major advantage of the tutor of the present invention is that it provides the patient's wrist with good postoperative mobility, both for flexion and extension movements, as well as for pronosupination, once the same has been fitted. This allows the patient, for example, to pour water from a receptacle or to drink water from a glass, and to perform these types of movements on a gentle basis. It is evident that it is an early mobility if compared to conventional treatments for the same purpose (plasters, tutors bridging the articulation, etc.) wherein an absolute immobility is required throughout the zone of influence for long periods of time. The characteristic of the tutor of the invention provides the patient with relative comfort throughout the whole therapeutical treatment and also decreases reflex sympathetic phenomena and osteoporosis risks.

Essentially, the invention refers to a monoplanar tutor, the dimensions of which are about 70 mm long per 10 mm wide and 5 mm thick, comprising a planar head articulated to a support body by means of a transverse screw, with respect to which said head may rotate and be fixed in the position chosen by the physician.

The novelty lies in that both the head and the body have transverse orifices run through by longitudinal pins which position the fractured bone portions in the correct place, with the particular feature that, due to the construction design of the tutor, the pins used and the tutor form a triangle which is very stable and safe.

To that effect, the transverse orifices of the articulated head have a 45° inclination with respect to the tutor's axis, while the body preferably has two or three orifices, two of which are perpendicular to the axis and the third one which may have a relative inclination so as to allow the utilization of any additional pin that will support any bone fragment that has remained unfixed by the others. Each of said orifices run through by the faces a perpendicular orifice where there are respective headless fastening screws; said screws exert pressure upon the pins, thus providing a retention action by means of a removable frictional adjustment.

Consequently, in order for the invented tutor to fit the patient, the following must be done: the patient is placed in a dorsal decubitus position, he is anaesthetized and then the "Zockowlosky" apparatus pulls on the limb, a free countertraction is applied from the elbow, using a 5 Kg weight, and this allows to perform manual reduction movements. Subsequently, the first pin is run through, and for that purpose it is convenient to use an image intensifier or Rx controls (which is much more simple than the image intensifier). Consequently, the first pin is put into position in a 45° angle from the radius styloid apophysis; the fracture focus is internally pierced and then it penetrates the internal cortical of the radius proximal end.

Upon the penetration of the first pin, the tutor is mounted and fitted using its distal orifice, so that it will be run through by said pin, leaving the tutor one centimeter away from the user's skin in order to avoid decubitus. Then the second pin is placed, penetrating the most proximal orifice of the tutor's body, which operates as a guide since it is perpendicularly oriented respect to the plate and to the radius.

Once the steps mentioned above have been completed, it is possible to finally fix the tutor using the rest of the passing orifices as a guide for the placement of the remaining pins, which is very simple. If there is a front or a rear fragment or a "Die Punch" fragment, it is reduced and then the remaining orifice in the tutor's body is used to place the sixth pin.

The stable fixing of the tutor is achieved by adjusting every screw facing the orifices through which pins penetrate, and by the transverse screw acting as an axis that articulates the tutor's head, and Rx controls are performed.

The tutor thus described is particularly suited for treating extra-articular fractures as well as non displaced intra-articular fractures.

The above mentioned characteristic pointing out that the tutor's head is articulated to the body thereof, so that it can be turned until adopting the selected position, before being adjusted and fixed, allows pins to be adapted to different orientation angles either towards the radius or away from it.

Once the tutor has been finally mounted, the structure defined in conjunction with the pins has a triangular form which, from a physical and mechanical point of view, is the rigid structure that best tolerates the different mechanical requirements to which it may be subjected.

To complete the advantages briefly described above, and many others that may be conceived by users and people skilled in the art, and to facilitate the understanding of the constructive, constitutive and functional characteristics of the external tutor of the invention, two preferred embodiments schematically illustrated regardless of a specified scale are described below with reference to, on the enclosed drawings. Accordingly, the scope of the present invention should be assessed as that of the appended claims.

BRIEF DESCRIPTION OF THE DRAWINGS

FIG. 4 is a side view that schematically shows the tutor of FIG. 1, once it has been fixed on a determined user.

FIG. 5 is a side view of a second embodiment of the present invention, representing the case wherein a higher amount of pins is required.

DETAILED DESCRIPTION OF THE PREFERRED EMBODIMENTS

The same numerals are assigned to the same or similar components of the assembly throughout the drawings, pursuant to the examples selected for the description of the tutor of the two embodiments of the present invention.

As it may be appreciated on the figures, the external tutor referred to in the present invention is a rigid piece comprising a main body -1- and a head -2- articulated thereto.

Figure 1:
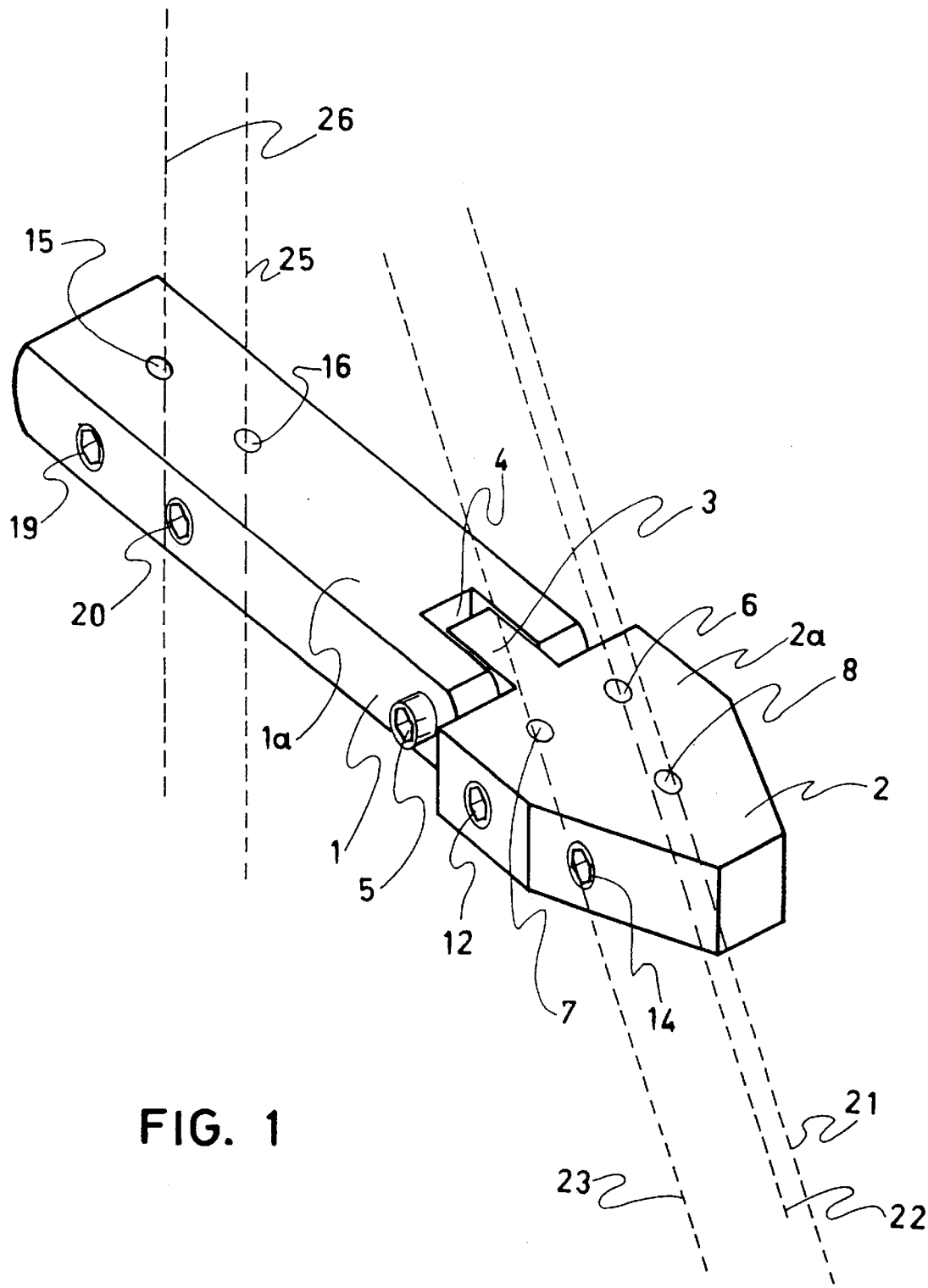
FIG. 1 is a perspective view showing a first embodiment of the external tutor of the invention as an assembly.
Figure 2:
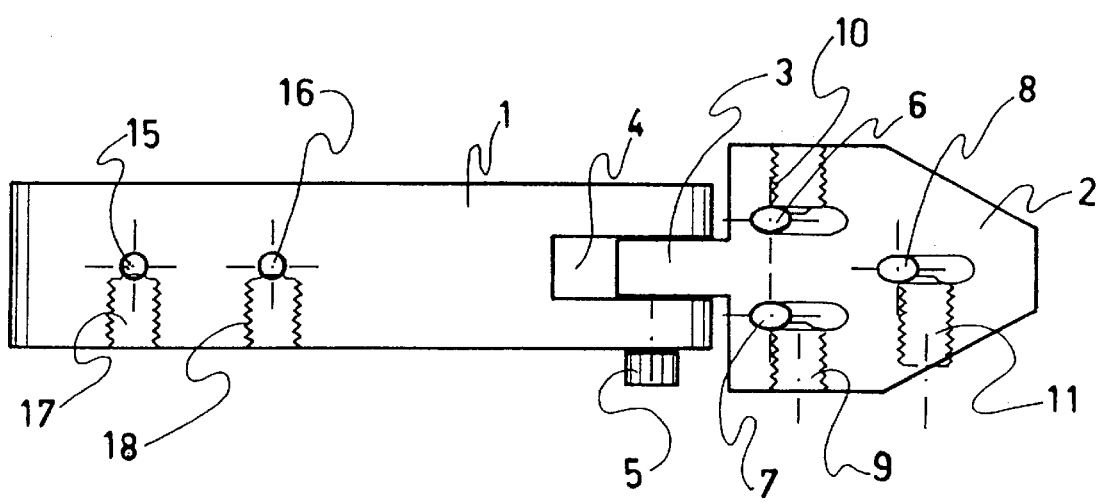
FIG. 2 is a top planar view of the tutor of FIG. 1.
Figure 3:
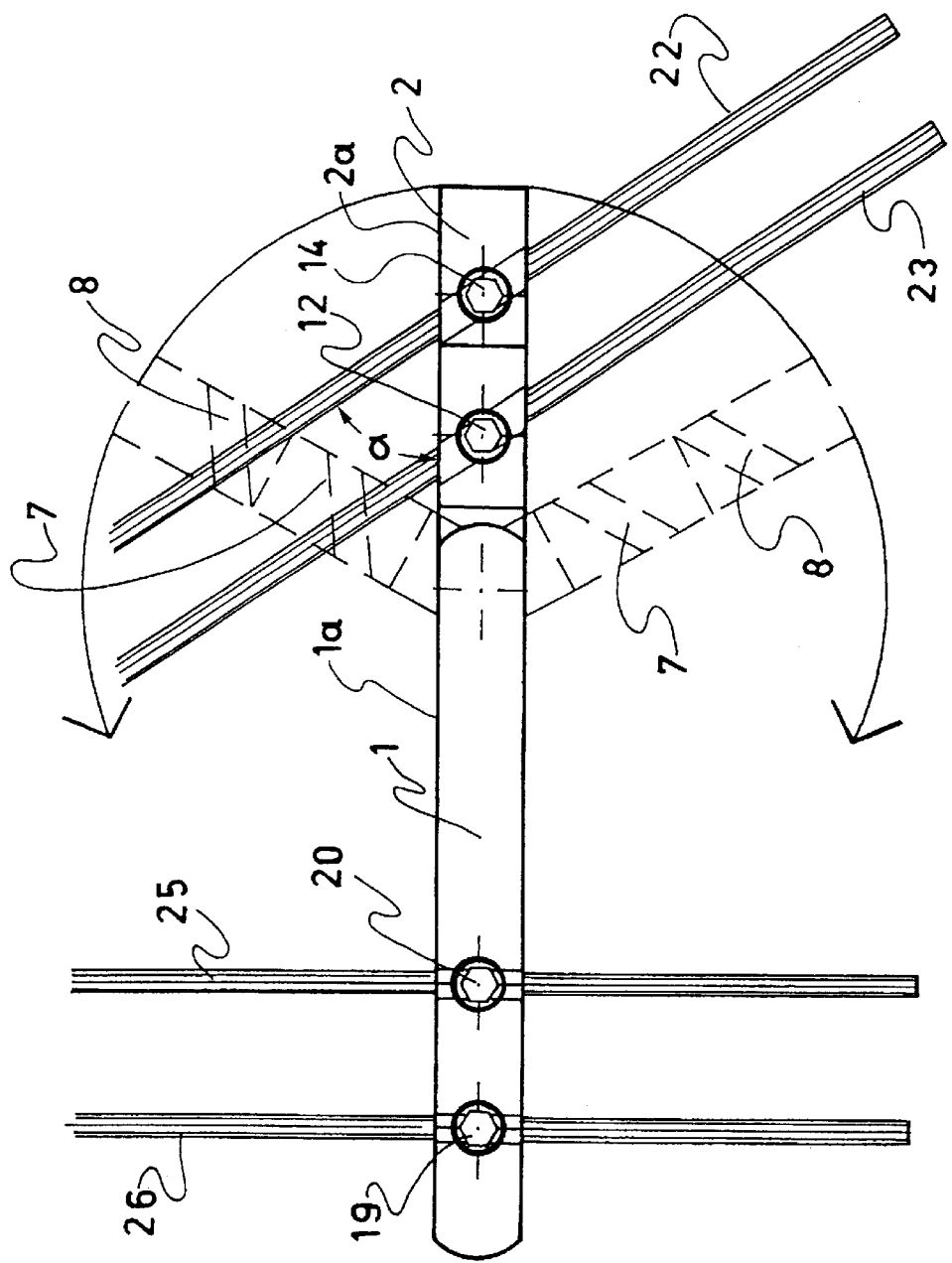
FIG. 3 is a side view of the tutor of FIG. 1, wherein the rotating capacity of the head is shown respect to the body of the same tutor.

For the articulation referred to above, a projection -3- of head -2- is lodged within an aperture -4- defined at the proximal end of the body, with the presence of a transverse orifice where the fitting-up screw -5- acts. Thus, said head -2- may rotate or turn respect to body -1-, (as shown in FIG. 3), until adequately positioning for the 45° angle a penetration of pins respect to the longitudinal axis of body -1-.

The head -2- referred to above includes passing orifices -6-, -7- and -8- which are skewed respect to a main planar surface 2a and the perpendicular transverse axis (now shown), and which are located inside the body thereof, with threaded orifices -9-, -10- and -11-, located in a horizontal plane, where pressure fitting-up screws referenced as -12-, -13- and -14- act.

On the other hand, said body -1- also has passing orifices -15- and -16- extending substantially perpendicular to main planar surface 1a and has matching respective threaded orifices -17- and -18- where pressure fitting-up screws -19- and -20- act.

From the observation of these drawings, it arises that said orifices -6-, -7- and -8- in head -2- are designed to be run through and to retain pins -21-, -22- and -23- which fix the fractured portions of radius -24-; while orifices -15- and -16- are designed to be run through and to retain pins -25- and -26- used to fix the tutor assembly on a stable basis and under the required conditions.

With reference now to FIG. 4, it is possible to clearly understand how the tutor of the invention operates for treating this type of fractures. A triangular composition is defined, pursuant to a right triangle wherein pins define the hypotenuse and one of the sides. Therefore, an undeformable structure is formed, said structure being very stable and resistant, preventing the occurrence of undesired relative movements in the fractured portions.

As it may be appreciated in FIG. 5, a second embodiment of the invention contemplates the use of an additional pin -27-, if necessary, for stabilizing some additional bone fragment -28-. Said pin is fixed and withheld to body -1- without affecting the normal operation of the specified structure.

As observed in the figures, every fitting-up screw remains wholly lodged within the orifices or threaded conduits wherein they act, thus preventing undue adjustment or disadjustment problems caused by external friction.

What is claimed is:

1. An external tutor suitable for treating fractures in the radius distal end using a plurality of pins that are inserted in the radius bone structure, the tutor comprising;
   a body defining a main planar surface and at least one orifice extending through the body substantially perpendicular to the main planar surface, each orifice for receiving a respective one of the pins;
   a head articulated to the body and defining a main planar surface orientable substantially parallel to the main planar surface of the body, the head further defining at least one orifice extending therethrough at an angle oblique to the main planar surface of the head, each orifice for receiving a respective one of the pins; and
   a plurality of threaded orifices extending laterally into the body and head, each threaded orifice communicating with a respective one of the orifices; and
   a plurality of screws threadable into the threaded orifices so that when the respective one of the pins is inserted into the respective one of the orifices, a respective one of the screws may be threaded into a respective one of the threaded orifices to fix the respective one of the pins relative to the respective one of the orifices.

2. An external tutor as claimed in claim 1, wherein the head has a proximal extension lodged into a defined cavity of the body, both sections being run through by a fitting-up screw, which acts as a transverse axis of articulation.

3. An external tutor as claimed in claim 2, wherein the fitting-up screw acts as a transverse axis of articulation of the head relative to the body, and extends substantially parallel to the main planar surfaces of the body and the head.

4. An external tutor as claimed in claim 1, wherein the angle oblique to the main planar surface of the head is 45°.

5. An external tutor as claimed in claim 1, wherein a rigid, substantially triangular structure is defined by the pins, the body and the head.

6. An external tutor as claimed in claim 5, wherein the rigid substantially triangular structure forms a right triangle.

* * * * *